United States Patent [19]
Felde et al.

[11] Patent Number: 5,801,428
[45] Date of Patent: Sep. 1, 1998

[54] MOS TRANSISTOR FOR BIOTECHNICAL APPLICATIONS

[75] Inventors: Andreas Vom Felde; Emmerich Bertagnolli; Martin Kerber, all of Munich, Germany

[73] Assignee: Siemens Aktiengesellschaft, Munich, Germany

[21] Appl. No.: 864,822

[22] Filed: May 29, 1997

[30] Foreign Application Priority Data

Jun. 12, 1996 [DE] Germany .................. 196 23 517.0

[51] Int. Cl.⁶ .................................................. H01L 27/14
[52] U.S. Cl. ..................... 257/414; 257/632; 257/640
[58] Field of Search ........................... 257/414, 632, 257/640

[56] References Cited

U.S. PATENT DOCUMENTS 4,005,455  1/1977  Watrous, Jr. et al. ................ 357/71
4,437,969  3/1984  Covington et al. ................... 204/403
4,508,613  4/1985  Busta et al. ........................... 204/418
4,921,591  5/1990  Mochizuki et al. ................... 203/412

FOREIGN PATENT DOCUMENTS 2 724 489A  3/1996  France .
39 40 540 A  6/1990  Germany .

OTHER PUBLICATIONS

Patent Abstracts of Japan, vol. 9, No. 210(p.–383), 28 Aug. 1985 & JP 60-073352 dated 25 Apr. 1985, Hitachi Ltd., Chemical FET Sensor, 1 page.

Primary Examiner—Sara W. Crane
Attorney, Agent, or Firm—Hill & Simpson

[57] ABSTRACT

An MOS transistor has a gate electrode is electrically conductively connected to an exposed contact area (pad). The contact area is electrochemically corrosion-resistant and is dimensioned for connection to a living cell. The surface topology is relatively flat and the surface, with the exception of the contact area, is protected with a dielectric passivation layer.

18 Claims, 1 Drawing Sheet

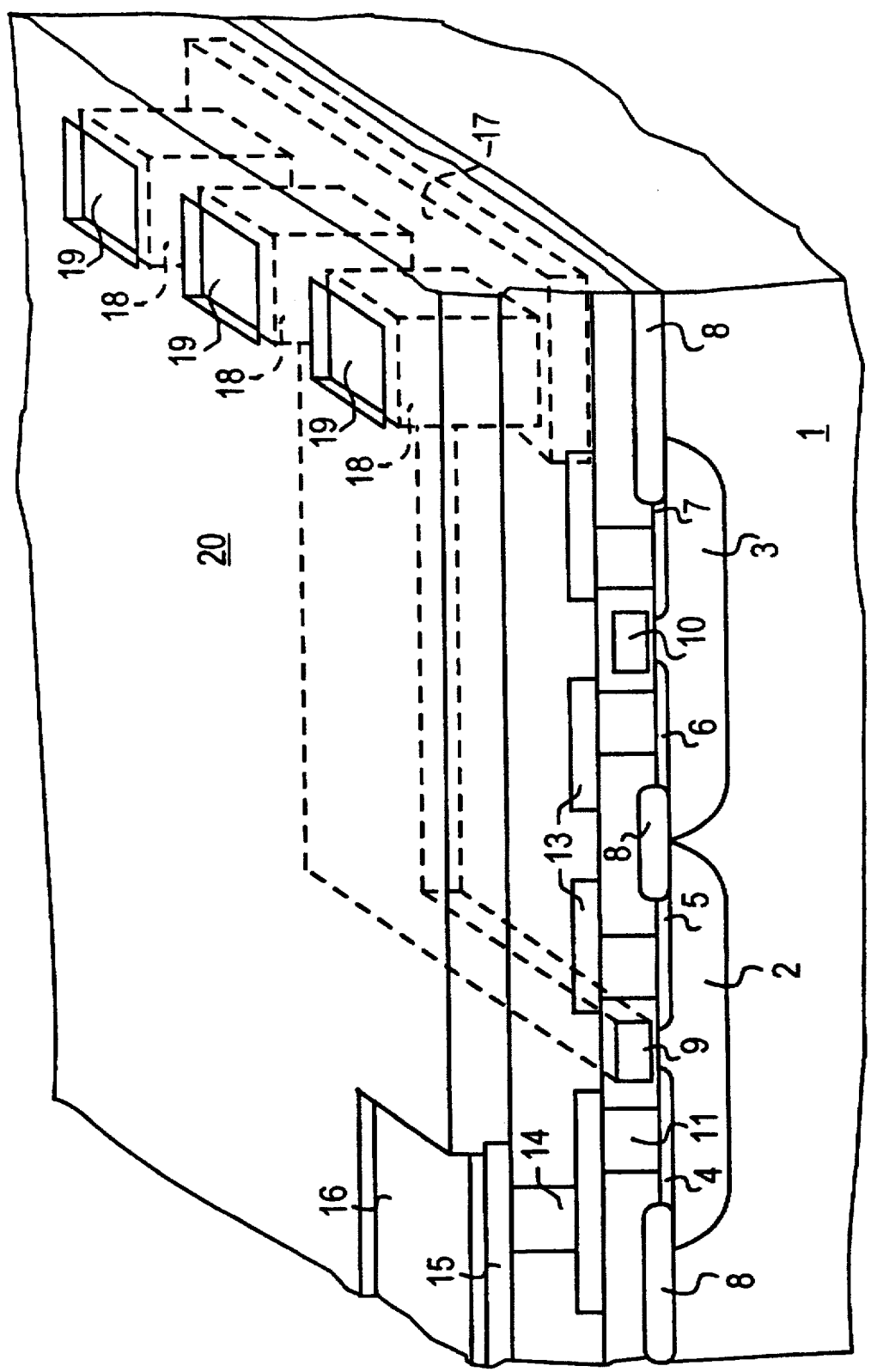

MOS TRANSISTOR FOR BIOTECHNICAL APPLICATIONS

BACKGROUND OF THE INVENTION

The recording of electrical activity and electrical stimulation of living neuron cells is a precondition for the investigation of biological mechanisms, in particular in the forwarding of nerve impulses, the detection of neurons and the learning ability of nerve tissue. Knowledge of this type forms the foundation for the future construction of neural biosensors and the realization of neuro-electronic circuits. The electrical coupling of living neuron cells to MOS transistors is currently the subject-matter of investigations. An electrically conductive connection between a cell membrane and the gate electrode of a MOS transistor is possible if a transistor is used without gate polysilicon and without a metallization layer. A problem associated with the use of semiconductor components for investigations of this type is the lack of resistance of many materials used for these components to the nutrient solutions used for the living cells. These nutrient solutions form an electrolyte which electrochemically erodes many materials.

SUMMARY OF THE INVENTION

It is an object of the present invention to provide a MOS transistor which is suitable for biotechnical applications and, in particular, is electrochemically corrosion-resistant.

The transistor according to the present invention has a gate electrode, which is electrically conductively connected to a contact area or terminal area (pad). This contact area is dimensioned for the relevant biotechnical application. It has, for example, dimensions matched to the size of a biological cell which is to be connected to the gate of the transistor in a conductive manner. This contact area is produced from a material which is electrochemically corrosion-resistant, in other words is not attacked either by the cell membrane or by a nutrient solution or an adhesive which establishes the contact. The remaining surface of this transistor is covered with a passivation layer, which leaves essentially only this contact area exposed and is resistant to the electrolytes to which the transistor is exposed in the application. A thin deposition of a nitride can be used, in particular, for a passivating covering layer of this type. A further property of the transistor according to the present invention is a relatively flat surface, that is to say the surface topology, at least in the region around the contact area, has height differences of at most 200 nm. This makes it easier to couple cells to the contact area.

In particularly preferred embodiments of the transistor according to the present invention, the ratio of gate width to gate length is greater than 3. The gate length is the dimension of the gate electrode in the direction from the source to the drain. The gate width is the dimension of the gate electrode at right angles to the gate length in a region around the channel which is necessary for the functioning of the transistor. This additional optimization makes it possible to achieve a maximum gradient of the characteristic curves of the transistor. In this way, the transistor affords a sufficiently high sensitivity to transform changes in the gate potential of 40 mV into changes in the drain current in the micro ampere range, even in the event of spontaneous activity of the nerve cells to be investigated (changes in the intracellular potential of about 40 mV to 60 mV).

In a further particularly preferred embodiment, the ratio of the area (surface area) of the contact area to the area of the gate electrode (the area of the gate web in plan view, the gate length multiplied by the gate width) is greater than 5. The effect achieved by this is that the gate electrode has a significantly smaller capacitance with respect to the substrate than a cell membrane of a biological cell applied to the contact area. The capacitances of the cell membrane and of the transistor then form an optimized capacitive voltage divider which permits a maximum amount of the voltage swing of the cell membrane to be transmitted to the gate in the active transistor region. This property is supported by a minimization of the area of the gate electrode (gate width ×gate length) in order to keep the capacitance of the gate electrode with respect to the substrate as small as possible. For cell membranes of small dimensions, the contact area can then likewise be kept small.

The gate electrode, the contact area and the electrically conductive connection between them are preferably produced from polysilicon in the context of a CMOS process. In such a process, it is possible to integrate further circuit components for evaluating measurement signals together with the transistor according to the present invention on a substrate. The polysilicon is provided with a metal siliconization, for example. When a metal is applied to the polysilicon, the metal is partially alloyed into the silicon and forms a special type of chemical compound with the silicon. Such a siliconization, as is also produced in the case of other components, can preferably be realized with titanium in the case of the transistor according to the present invention. Besides titanium, it is also possible to use other siliconizable metals, for example tantalum, tungsten, cobalt, molybdenum, platinum or palladium, which are likewise sufficiently corrosion resistant and suitable for a connection to biological organisms.

Instead of such a siliconization, or supplementary thereto, a complete (for example multilayer) metallization may be present. For this, use is made particularly of tungsten as the metal for the surface of the contact area, for the electrically conductive connection to the gate electrode and for the metallization of the gate electrode. In particular, the electrically conductive connection to the components of an integrated electronic circuit can also be realized by a metallization of this type. In the case of a metallization of this type, the conduction resistances are significantly smaller than in the case of the suicides. In addition to tungsten, it is also possible to use for these metallizations titanium, tantalum, cobalt, molybdenum, platinum, iridium, palladium and TiN or combinations of these materials.

The passivating covering layer, which covers the top side of the transistor with the exception of the contact area, is preferably a thin nitride layer (for example SiN), which is preferably applied by means of CVD to a thickness of at least 50 nm and at most 250 nm. In this way, low ratios of depth to diameter of the contact point are realized in the region of the contact area. This so-called aspect ratio of the contact point is an important parameter which determines the strength of the coupling between the cell membrane and the transistor.

With gate widths in the sub-micrometer range and with gate-to-gate spacings of less than 10 μm, it is possible to realize arrays of transistors according to the present invention with which a high spatial resolution can be achieved. As a result they can also be used to investigate larger nerve cells of more highly developed organisms.

Typical dimensions of the transistor according to the present invention given the current state of production technologies are, for example, a gate length of about 0.8 μm and a gate width of 5.0 μm. The contact area can have a size of 10 μm×10 μm, for example. However, it is also possible to realize contact areas which are optimized for cell membranes having a diameter of 1 μm.

BRIEF DESCRIPTION OF THE DRAWINGS

The features of the present invention which are believed to be novel,are set forth with particularity in the appended claims. The invention, together with further objects and advantages, may best be understood by reference to the following description taken in conjunction with the accompanying drawings, and in which:

The single FIGURE depicts an MOS transistor according to the present invention.

DESCRIPTION OF THE PREFERRED EMBODIMENTS

The single FIGURE illustrates a possible exemplary embodiment of the transistor according to the present invention. As depicted in the single FIGURE n-type wells and/or p-type wells 2, 3, in which doped regions 4, 5, 6, 7 are present as source and drain regions of MOSFETS, are situated in a substrate 1, which is silicon, for example. An n-type well 2 can be provided, for example, for the transistor according to the present invention, which is illustrated on the left in the single FIGURE. A further MOSFET, which is complementary thereto, is formed in a p-type well 3, for example. The regions of the source 4 and the drain 5 of the transistor according to the present invention are then p-conducting. The regions of the source 6 and the drain 7 of the transistor complementary thereto are then n-conducting. The transistors illustrated are to be understood only as an example. A fundamentally unlimited number of MOSFETs which are produced in the context of the CMOS process can be integrated on the substrate 1.

Between these transistors there are situated insulating regions 8, which are produced by thermal oxidation (LOCOS) for example. The gate electrode 9 is applied to the gate oxide in the region of the channel of the transistor according to the present invention. As shown by the concealed contours illustrated by dashed lines, the gate electrode 9 is routed laterally to a larger terminal area 17, to which blocks or pillars 18 are applied after the manner of contact hole fillings. The gate electrode 9 is preferably polysilicon. A corresponding gate electrode 10, which, however can be connected, for example via the metallization planes 13 provided, to a circuit integrated on the substrate 1, is provided for the further MOSFET. Vertical conductive connections 11, 12, which are produced, for example, as contact hole fillings over the source and drain regions to be connected, are situated in a first dielectric layer. As is customary, this first dielectric layer is preferably boron phosphorus silicate glass BPSG), for example. One or more further dielectric layers (intermediate oxide, IMOX) can be provided over the metallization plane 13, which is structured to form terminal contacts or conductor tracks. Further vertical electrically conductive connections 14 are formed in the further dielectric layers. The illustrated connection 14 leads to a terminal area 15 on the top side which is covered by a corrosion resistant metallization layer 16. The top sides 19 of the blocks or pillars 18 on the terminal area 17 of the gate electrode 9 are likewise composed of corrosion-resistant material. The pillars 18 may be composed completely of this corrosion-resistant material and are then produced as contact hole fillings, for example. However, in principle it suffices if the outwardly exposed top side 19 is electrochemically corrosion-resistant. The top sides 19 of these pillars 18 are provided for applying neuron cells in a nutrient solution to them, and are therefore correspondingly dimensioned. The terminal area 15 with the electrochemically corrosion-resistant metallization layer 16 is provided, for example, as a terminal contact for a measurement (measurement pad). The top side 20 of the arrangement is formed by the passivating covering layer, which is preferably a thin nitride layer (CVD nitride) and which, as described above, projects only slightly above the top sides 19 to which the neuron cells are to be applied.

The entire top side of the gate electrode 9, of the terminal area 17 and of the connection arranged in between can be provided with a metallization layer. If a material which is resistant to the nutrient solution of the neuron cells is used for this metallization layer, it is possible to dispense with the pillars 18 and to apply the neuron cells in a corresponding cutout in the passivation layer directly to this metallization layer covering the terminal region 17. The pillars 18 can have a smaller lateral dimension than is illustrated in the single FIGURE. It suffices if contact areas having a surface area which is sufficient for the size of the neuron cells and having a corrosion-resistant surface are present. The surfaces 19 provided for the application of the neuron cells can then be applied, for example, to terminal contacts which correspond to the measurement terminal contact 15, illustrated on the left in the single FIGURE, and are connected via a relatively thin contact hole filling, corresponding to the connection 14 on the left-hand side, to the terminal area 17. The pillars 18 can also be formed from silicon (polysilicon or amorphous silicon) instead of from metal. Further details of the transistor according to the present invention, which have not been illustrated for the sake of clarity, essentially correspond to the details which are known for transistors produced in the context of a CMOS process.

The invention is not limited to the particular details of the apparatus depicted and other modifications and applications are contemplated. Certain other changes may be made in the above described apparatus without departing from the true spirit and scope of the invention herein involved. It is intended, therefore, that the subject matter in the above depiction shall be interpreted as illustrative and not in a limiting sense.

What is claimed is:

1. An MOS transistor comprising:
    a gate electrode and a contact area which is electrically conductively connected to said gate electrode;
    said contact area being electrochemically corrosion-resistant;
    said contact area having a difference in height of at most 200 nm relates to an outer surface surrounding the contact area; and
    said surface surrounding the contact area having a passivating covering layer.

2. The MOS transistor according to claim 1, wherein the MOS transistor further comprises a gate and wherein a ratio of gate width to gate length of said gate is greater than 3.

3. The MOS transistor according to claim 1, wherein a ratio of the surface area of the contact area to the surface area of the gate electrode is greater than 5.

4. The MOS transistor according to claim 1, wherein said gate electrode, said contact area and an electrically conductive connection therebetween are polysilicon which is siliconized with a metal from a group consisting of titanium, tantalum, tungsten, cobalt, molybdenum, platinum and palladium.

5. The MOS transistor according to claim 1, wherein the gate electrode, the contact area and an electrically conductive connection therebetween are provided with a metallization layer which consists of at least one material from a group consisting of tungsten, titanium, tantalum, cobalt, molybdenum, platinum, iridium, palladium and TiN.

6. The MOS transistor according to claim 1, wherein the covering layer is a nitride and has a thickness in the range of 50 nm to 250 nm.

7. The MOS transistor according to claim 1, wherein the MOS transistor further comprises a gate and wherein a gate width multiplied by a gate length of the gate is greater than 5.

8. An MOS transistor comprising:

a gate electrode and a contact area which is electrically conductively connected to said gate electrode;

said contact area being electrochemically corrosion-resistant;

said contact area having a difference in height of at most 200 nm relates to an outer surface surrounding the contact area;

said surface surrounding the contact area having a passivating covering layer; and a gate, a ratio of gate width to gate length of said gate being greater than 3.

9. The MOS transistor according to claim 8, wherein a ratio of the surface area of the contact area to the surface area of the gate electrode is greater than 5.

10. The MOS transistor according to claim 8, wherein said gate electrode, said contact area and an electrically conductive connection therebetween are polysilicon which is siliconized with a metal from a group consisting of titanium, tantalum, tungsten, cobalt, molybdenum, platinum and palladium.

11. The MOS transistor according to claim 8, wherein the gate electrode, the contact area and an electrically conductive connection therebetween are provided with a metallization layer which consists of at least one material from a group consisting of tungsten, titanium, tantalum, cobalt, molybdenum, platinum, iridium, palladium and TiN.

12. The MOS transistor according to claim 8, wherein the covering layer is a nitride and has a thickness in the range of 50 nm to 250 nm.

13. The MOS transistor according to claim 8, wherein the MOS transistor further comprises a gate and wherein a gate width multiplied by a gate length of the gate is greater than 5.

14. An MOS transistor comprising:

a gate electrode and a contact area which is electrically conductively connected to said gate electrode;

said contact area being electrochemically corrosion-resistant;

said contact area having a difference in height of at most 200 nm relates to an outer surface surrounding the contact area;

said surface surrounding the contact area having a passivating covering layer, the covering layer being a nitride and having a thickness in the range of 50 nm to 250 nm;

a ratio of the surface area of the contact area to the surface area of the gate electrode being greater than 5.

15. The MOS transistor according to claim 14, wherein the MOS transistor further comprises a gate and wherein a ratio of gate width to gate length of said gate is greater than 3.

16. The MOS transistor according to claim 14, wherein said gate electrode, said contact area and an electrically conductive connection therebetween are polysilicon which is siliconized with a metal from a group consisting of titanium, tantalum, tungsten, cobalt, molybdenum, platinum and palladium.

17. The MOS transistor according to claim 14, wherein the gate electrode, the contact area and an electrically conductive connection therebetween are provided with a metallization layer which consists of at least one material from a group consisting of tungsten, titanium, tantalum, cobalt, molybdenum, platinum, iridium, palladium and TiN.

18. The MOS transistor according to claim 14, wherein the MOS transistor further comprises a gate and wherein a gate width multiplied by a gate length of the gate is greater than 5.

* * * * *